United States Patent [19]

Beck et al.

[11] Patent Number: 4,610,999

[45] Date of Patent: * Sep. 9, 1986

[54] 4-SUBSTITUTED Δ2-IMIDAZOLINYL-THIOETHERS WITH PROSTAGLANDIN-LIKE ACTIVITY

[75] Inventors: Gerhard Beck, Frankfurt am Main; Wilhelm Bartmann; Hans-Hermann Laü, both of Bad Soden am Taunus; Günther Wess, Erlensee, all of Fed. Rep. of Germany

[73] Assignee: Hoechst Aktiengesellschaft, Fed. Rep. of Germany

[*] Notice: The portion of the term of this patent subsequent to Sep. 9, 2003 has been disclaimed.

[21] Appl. No.: 659,772

[22] Filed: Oct. 11, 1984

[30] Foreign Application Priority Data

Oct. 13, 1983 [DE] Fed. Rep. of Germany ....... 3337181

[51] Int. Cl.$^4$ .................. A61K 31/415; C07D 233/42
[52] U.S. Cl. .................................. 514/401; 514/402; 548/348; 548/351
[58] Field of Search ................ 548/351, 348; 514/401, 514/402

[56] References Cited

U.S. PATENT DOCUMENTS 4,308,277 12/1981 Ferrini et al. ...................... 548/351
4,496,577 1/1985 Muchowski et al. ........... 548/321 X

FOREIGN PATENT DOCUMENTS 0008073 2/1980 European Pat. Off. ............ 548/351

OTHER PUBLICATIONS

Bartmann, W., et al., *Angew. Chem. Ed. Engl.,* 21 (1982), pp. 751–764.

*Primary Examiner*—Richard A. Schwartz
*Attorney, Agent, or Firm*—Finnegan, Henderson, Farabow, Garrett & Dunner

[57] ABSTRACT

The present invention relates to 4-substituted Δ2-imidazolinyl-thioethers and to intermediates and processes for their preparation. The components according to the invention are distinguished in particular by their platelet aggregation-inhibiting and hypotensive action.

13 Claims, No Drawings

4-SUBSTITUTED Δ2-IMIDAZOLINYL-THIOETHERS WITH PROSTAGLANDIN-LIKE ACTIVITY

Prostacyclin $PGI_2$, a natural substance isolated in 1976 and belonging to the prostaglandin family, is distinguished by its highly pronounced platelet aggregation-inhibiting properties (The Lancet 1977, 18). $PGI_2$ is also capable of relaxing some blood vessels, for example coronary arteries (Prostaglandins 13, 3, 1977), so that it can be used for the therapy and prophylaxis of thromboses and infarctions. $PGI_2$ also has a pronounced hypotensive action (for example IRCS Med. Sci. 6, 392 (1978)).

The present invention relates to novel compounds of the general formula I

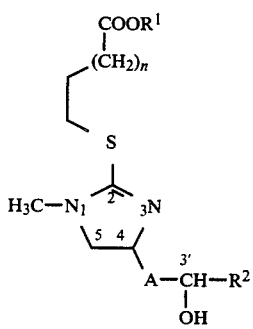

which have a specific action and/or a longer-lasting action than $PGI_2$, and
in which:

$R^1$ denotes hydrogen, a straight-chain or branched alkyl radical with up to 8 carbon atoms, a straight-chain or branched unsaturated aliphatic hydrocarbon radical with 3 to 6 carbon atoms, a cycloaliphatic hydrocarbon radical with 3 to 7 carbon atoms, an araliphatic hydrocarbon radical with 7 to 9 carbon atoms or a physiologically acceptable metal ion, $NH_4$ ion or an ammonium ion which is derived from a primary, secondary or tertiary amine, or a tetraalkylammonium ion, $R^2$ denotes a phenyl radical, which can be mono-, di- or tri-substituted in the nucleus by halogen, trifluoromethyl and/or alkyl or alkoxy with in each case 1-6 carbon atoms, or denotes a cycloaliphatic radical with 3-8 carbon atoms, a straight-chain or branched alkyl radical with up to 8 carbon atoms or a straight-chain or branched unsaturated aliphatic hydrocarbon radical with 3 to 8 carbon atoms, it being possible for the aliphatic radicals in turn to be substituted by (a) a straight-chain or branched alkoxy radical with up to 6 carbon atoms or a straight-chain or branched alkenyloxy or alkinyloxy radical with 3 to 6 carbon atoms, (b) halogen, cycloalkyl with 3-7 carbon atoms, an unsubstituted phenyl, α- or β-thienyl or α- or β-furyl radical or a phenyl, thienyl or furyl radical which is in turn mono-, di- or tri-substituted in the nucleus by halogen, trifluoromethyl and/or alkyl or alkoxy with 1-6 carbon atoms, (c) an unsubstituted phenoxy, α- or β-thienyloxy or cycloalkoxy radical with 3-7 carbon atoms, or one of the radicals mentioned, which is in turn mono-, di- or tri-substituted in the nucleus by halogen, trifluoromethyl and/or alkyl or alkoxy with in each case 1-6 carbon atoms, n denotes the number 0, 1, 2, 3 or 4 and A denotes a —CH=CH— or —$CH_2$—$CH_2$ group.

Preferred substituents $R^1$ are: hydrogen, straight-chain or branched alkyl with up to 8 carbon atoms, in particular $C_1$–$C_4$-alkyl, a straight-chain or branched, unsaturated aliphatic hydrocarbon radical with up to 4 carbon atoms, in particular $C_2$–$C_4$-alkenyl, a cycloaliphatic hydrocarbon radical with 5–7 carbon atoms, in particular $C_5$–$C_7$-cycloalkyl, an araliphatic hydrocarbon radical with 8 or 9 carbon atoms, in particular phenethyl or benzyl, or an ammonium ion which is derived from a primary, secondary or tertiary amine, for example hydrogen, methyl, ethyl, n-butyl, n-pentyl, n-hexyl, n-heptyl, 2-propyl, 2-butyl, 2-pentyl, 3-hexyl, 2-methylpropyl, 2-methylbutyl, 4,4-dimethylpentyl, 5,5-dimethylhexyl, cyclopentyl, cyclohexyl, cycloheptyl, methylammonium, dicyclohexylammonium or tris-(hydroxymethyl)-methylammonium.

The substituents $R^2$ listed below are particularly preferred:

unsubstituted phenyl or phenyl which is monosubstituted by halogen, trifluoromethyl, $C_1$–$C_4$-alkyl or $C_1$–$C_4$-alkoxy, or straight-chain or branched $C_3$–$C_7$-alkyl, which can be substituted by optionally substituted $C_5$–$C_7$-cycloalkyl, by $C_1$–$C_3$-alkoxy, by phenoxy or halogenophenoxy, by thienyloxy or halogenothienyloxy, by cyclohexyloxy, by thienyl, by halogenothienyl or by furyl, in particular the radicals: n-pentyl, 1,1-dimethylpentyl, cyclopentylmethyl, cyclohexylmethyl, 1,1-dimethyl-2-ethoxyethyl, 1,1-dimethyl-2-methoxyethyl, 1,1-dimethylcyclohexyloxymethyl, 1-fluoropentyl, 1-chloropentyl, 5-fluoropentyl, 5-chloropentyl, 3-thienyl-2-ethyl, 2-thienyl-2-ethyl, 3-(2-chlorothienyl)-2-ethyl, 2-(5-chlorothienyl)-2-ethyl, phenoxymethyl, 3-chlorophenoxymethyl, 2-thienyloxymethyl, 3-(2-chlorothienyl)-oxymethyl, 2-(5-chlorothienyl)-oxymethyl, 3-furyl-2-ethyl, 2,2,3,3-tetrafluoro-cyclobutyl-2-ethyl, phenyl, 3-chlorophenyl and 3-tri-fluoromethylphenyl.

n preferably denotes 1 or 2.

The invention furthermore relates to a process for the preparation of the compounds of the formula I, which comprises (a) converting the imidazolidinone of the formula II

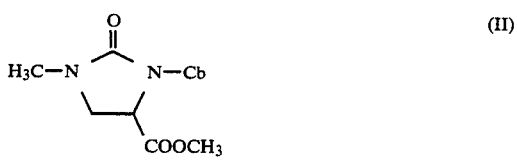

in which Cb denotes the radical

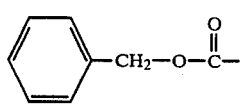

into the imidazolidinone-alcohol III

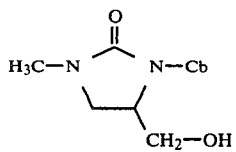
(III)

by reduction of the ester function, (b) oxidizing the compound of the formula III to give the enolized aldehyde of the formula IV

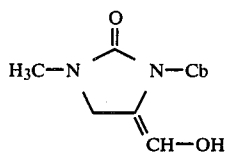
(IV)

(c) reacting the aldehyde of the formula IV with a phosphonate of the formula V

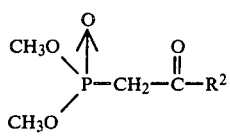
(V)

in which $R^2$ has the meaning given in the case of formula I, to give an enone of the formula VI

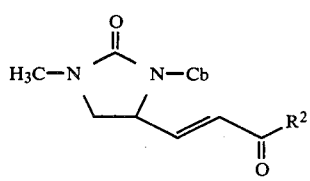
(VI)

in which $R^2$ has the meaning given in the case of formula I, (d) reducing the enone of the formula VI with a reducing agent in a known manner to give a 3'-epimer mixture of the alcohols of the formula VII, in which $R^2$ has the meaning given in the case of formula I, and, if appropriate, separating the resulting 3'-epimer mixture of the alcohols of the formula VII into the α- and β-epimers by customery methods

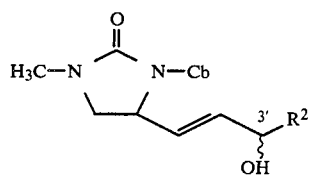
(VII)

(e) splitting off the Cb protective group on N atom (3) in the epimer mixture of the alcohols of the formula VII or in the pure α- or β-epimers by alkaline hydrolysis, a compound of the formula VIII

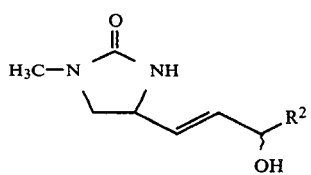
(VIII)

in which $R^2$ has the meaning given in the case of formula I, being obtained, or (e') hydrogenating the epimer mixture of the alcohols or the pure α- or β-epimers of the formula VII by customary methods to give a compound of the formula IX

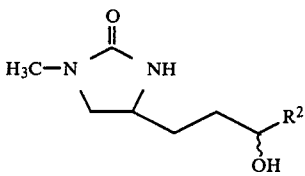
(IX)

in which $R^2$ has the meaning given in the case of formula I, (f) acylating a compound of the formula VIII or IX on the alcohol function to give a compound of the formula X

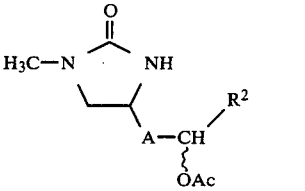
(X)

in which A represents a —CH=CH— or —CH$_2$—CH$_2$-group, Ac represents an alkanoyl, arylalkanoyl or cycloalkanoyl radical and $R^2$ has the meaning given in the case of formula I, (g) converting a compound of the formula X into a compound of the formula XI

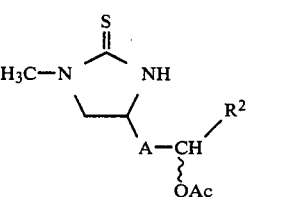
(XI)

in which A and $R^2$ have the meaning given in the case of formula I and Ac has the meaning given in the case of formula X, by sulfur-donating reagents by customary methods, (h) splitting off the protective group Ac in a compound of the formula XI by alkaline hydrolysis, a compound of the formula XII

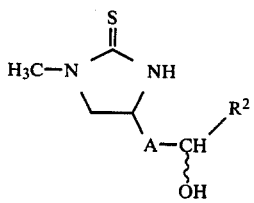

(XII)

in which A and R² have the meaning given in the case of formula I, being obtained, (i) reacting a compound of the formula XII with a compound of the formula XIII

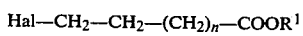

Hal—CH₂—CH₂—(CH₂)ₙ—COOR¹ (XIII)

in which R¹ and n have the meaning given in the case of formula I and Hal denotes iodine, chlorine or bromine to give a compound of the formula I, (k) if appropriate, hydrolyzing a compound of the formula I, in which R¹ is not hydrogen or a cation, to give a compound of the formula I in which R¹ denotes hydrogen or a physiologically acceptable cation, (l) if appropriate, replacing the cation R¹ in a compound of the formula I in which R¹ denotes hydrogen or a physiologically acceptable metal ion, NH₄ ion or ammonium ion which is derived from a primary, secondary or tertiary amine, and R² and n have the meanings given in the case of formula I, by another cation R¹.

The imidazolidinone II used as the starting material in the process according to the invention can be prepared by a process analogous to that which has been described by S. Saijo and coworkers in Chem. Pharm. Bull 28, 1,459 (1980).

The imidazolidine-alcohol of the formula III is obtained by reacting the imidazolidine ester of the formula II with a complex metal hydride, preferably an alkali metal boronate, such as sodium borohydride, potassium borohydride or lithium borohydride.

The oxidation of an alcohol of the formula III to give an aldehyde of the formula IV can be carried out by oxidizing agents, such as pyridinium chlorochromate, in inert solvents, such as methylene chloride or chloroform. Another oxidation possibility consists of the reaction with thioanisole/Cl₂/trimethylamine in carbon tetrachloride, or the reaction with dimethylsulfoxide/oxalyl chloride/NEt₃ at −20° C. The aldehyde of the formula IV is almost entirely in the enolized form.

In the subsequent step, the aldehyde of the formula IV is reacted with a phosphonic acid ester of the formula V by a Horner-Emmons-Wittig reaction to give an unsaturated ketone of the formula VI, a preferred embodiment comprising adding DBU (1,8-diazabicyclo-[5.4.0]-undec-7-ene) to the phosphonic acid ester of the formula V in dimethoxyethane and then adding the aldehyde of the formula VI and allowing the mixture to react at room temperature for 2-6 hours. The phosphonic acid esters of the formula V can be prepared by processes which are known from the literature (see, for example, J. Am. Chem. Soc. 88, 5,654 (1966)).

The compounds of the formula VII are obtained in the form of their epimer mixtures when an enone of the formula VI is reduced with a complex metal hydride, preferably with an alkali metal boronate or with D,L-isobornyloxyaluminum isopropoxide, preferably between −5° and +20° C. in methanol, ethanol or ethers, such as dimethoxyethane or tetrahydrofuran—if appropriate with the addition of water.

The compounds of the formula VIII are obtained by hydrolytic splitting-off of the protective group on N-3, preferably with alkali metal hydroxides, such as NaOH, KOH or LiOH, in alcohol-water mixtures at +5° to 30° C.

The acylation of the compounds of the formula VIII or IX is carried out in the generally customary manner with acyl halides (such as, for example, acetyl chloride, benzoyl chloride and the like) or with acid anhydrides (such as, for example, acetic anhydride, propionic anhydride and the like), in the presence of bases, such as pyridine, triethylamine and the like.

The compounds of the formula XI can be prepared from imidazolidinones of the formula X by reaction with sulfur-donating reagents, such as, for example, phosphorus pentasulfide, phosphorus pentasulfide/calcium oxide, a phosphorus pentasulfide-pyridine complex or a phosphorus pentasulfide-anisole complex in inert solvents, such as, for example, toluene, dimethoxyethane or pyridine, by methods which are known from the literature (see, for example, Bull. Soc. Chim. Belg. 87, (3), 229 (1978)).

The acyl protective group in the compounds of the formula X can be split off in the generally customary manner by alkaline or acid hydrolysis, but preferably by stirring with dry potassium carbonate in methanol at room temperature.

To prepare the compounds of the formula I, the imidazolidinethiones of the formula XII are reacted with the halides of the formula XIII. This reaction can be carried out in an inert solvent, for example toluene, diglyme, tetrahydrofuran, dimethoxyethane or dimethylformamide, in the presence of a base, such as, for example, pyridine, triethylamine, potassium carbonate or sodium hydride, at 15°-180° C. However, a preferred embodiment of this reaction comprises alkylating the compounds of the formula XII in absolute diglyme, without the addition of a base, with the compounds of the formula XIII at 70°-100° C. in the course of 1-6 hours and liberating the compounds of the general formula I from the NH-salts of the compounds of the general formula I intermediately formed, during working-up with aqueous NaHCO₃ solution.

Compounds of the formula I in which R¹ does not represent hydrogen or a cation can be hydrolyzed in an alkaline medium to give compounds of the formula I in which R¹ denotes hydrogen or a cation, for example using NaOH or KOH in a low-molecular weight alcohol, such as methanol, or in ethers, such as dimethoxyethane or tetrahydrofuran, if appropriate in the presence of water. However, the compounds of the formula I in which R¹ is hydrogen are advantageously prepared by alkylating the compounds of the formula XII with a compound of the formula XIII in which R¹ is hydrogen. Compounds of the formula I in which R¹ represents a cation are preferably obtained by reacting (neutralizing) the compounds of the formula I in which R¹=hydrogen with metal hydroxides, such as, for example, NaOH, KOH or LiOH, in aqueous solution and evaporating the solvent, preferably by freeze-drying.

The alkali metal cation can be replaced by any other cations on ion exchangers in the customary manner. For this, the solution of the alkali metal salt of an imidazolinyl-thioether, of the formula I, according to the invention is allowed to run through a column filled with a cation exchanger, such as, for example, ®Amberlite CG-50 or ®Dowex CCR-2. The cation exchanger is laden with the desired cation, for example with an ammonium ion which is derived from a primary, secondary or tertiary amine. The desired salt is obtained by evaporating the eluate.

Compounds of the formula I in which $R^1=NH_4$ or an ammonium ion which is derived from a primary, secondary or tertiary amine can also be prepared by adding an equimolar amount of the corresponding amine to compounds of the formula I, in which $R^1$ denotes hydrogen, in an alcoholic solution, and evaporating the solvent.

Compounds of the formula I in which $R^1$ denotes hydrogen or a cation can be esterified to give compounds of the formula I in which $R^1$ has the other meanings given in the case of formula I. Thus, for example, compounds of the formula I in which $R^1$=hydrogen can be esterified with a diazoalkane at temperatures between $-40°$ and $+20°$ C., it being possible to employ the usual solvents, such as, for example, diethyl ether, tetrahydrofuran, chloroform or low-molecular weight alcohols, such as methanol. The resulting esters can be isolated in a simple manner by evaporation of the solvent and, if appropriate, purified by chromatography. One esterification method comprises reacting salts of the compounds of the formula I ($R^1$=a cation) with an alkylating agent $R^1$-Z in the presence of a base, such as, for example, a metal alcoholate or metal carbonate, in a suitable solvent. Possible metal alcoholates are, for example, sodium methylate, sodium ethylate and potassium tert.-butylate, and a suitable carbonate is, for example, potassium carbonate. Possible suitable solvents are alcohols, such as, for example, methanol or tert.-butanol, ethers, such as tetrahydrofuran or 1,2-dimethoxyethane, and, in particular, dipolar aprotic solvents, such as dimethylformamide, dimethylsulfoxide and acetonitrile, or N-methylpyrrolidone. In the formula $R^1$-Z, Z preferably denotes bromine or iodine or a sulfonic acid radical. The method of transesterification with an excess of alcohols, such as, for example, methanol, ethanol or isopropanol, is also suitable for the preparation of esters of the formula I ($R^1$=alkyl).

The compounds of the formula I are obtained in the form of the racemate in respect of the position on carbon atom 5 of the imidazoline ring and as $\alpha/\beta$-isomers in respect of the carbon atom 3'. The $\alpha/\beta$-isomers are preferably separated at the stage of the end products of the formula I. The racemate in respect of the carbon atom 5 of the imidazoline ring can preferably be separated at the compounds of the formula VII, VIII or IX, or at the stage of the end products of the formula I. This means that all the reactions described can be carried out with epimer mixtures, pure epimers or optically active antipodes. The compounds claimed, of the formula I, thus include diastereomer mixtures, pure diastereomers, epimer mixtures and pure epimers.

If the individual reaction products are not already obtained in a sufficiently pure form so that they can be used for the subsequent reaction step, purification by means of, for example, column, thin layer or high-pressure liquid chromatography is advisable.

The following compounds can be prepared by the processes according to the invention, in addition to the compounds described in the examples: 1-methyl-2-(1-thia-5-carboxy-pentyl)-4-(3-hydroxy-1-octenyl)-Δ2-imidazoline, 1-methyl-2-(1-thia-4-carboxy-butyl)-4-(3-hydroxy-1-octenyl)-Δ2-imidazoline, 1-methyl-2-(1-thia-6-carboxyhexyl)-4-(3-hydroxy-1-octenyl)-Δ2-imidazoline, 1-methyl-2-(1-thia-4-methoxycarbonyl-butyl)-4-(3-hydroxy-1-octenyl)-Δ2-imidazoline, 1-methyl-2-(1-thia-5-methoxycarbonyl-pentyl)-4-(3-hydroxy-1-octenyl)-Δ2-imidazoline, 1-methyl-2-(1-thia-methoxycarbonyl-butyl)-4-(3-hydroxy-5-(2-furyl)-1-pentenyl)-Δ2-imidazoline, 1-methyl-2-(1-thia-4-methoxycarbonyl-butyl)-4-(3-hydroxy-4,4-dimethyl-4-cyclohexyloxy-1-butenyl)-Δ2-imidazoline, 1-methyl-2-(thia-4-methoxycarbonyl-butyl)-4-(3-hydroxy-3-phenyl-1-propenyl)-Δ2-imidazoline, 1-methyl-2-(1-thia-4-ethoxycarbonyl-butyl)-4-(3-hydroxy-4-(3-trifluoromethyl-phenyloxy)-1-butenyl)-Δ2-imidazoline, 1-methyl-2-(1-thia-4-cyclohexyloxycarbonyl-butyl)-4-(3-hydroxy-1-octenyl)-Δ2-imidazoline, 1-methyl-2-(1-thia-7-methoxycarbonyl-heptyl)-4-(3-hydroxy-1-octenyl)-Δ2-imidazoline, 1-methyl-2-(1-thia-4-ethoxycarbonyl-butyl)-4-(3-hydroxy-1-nonenyl)-Δ2-imidazoline, 1-methyl-2-(1-thia-4-methoxycarbonyl-butyl)-4-(3-hydroxy-1-decenyl)-Δ2-imidazoline, 1-methyl-2-(1-thia-5-carboxyl-pentyl)-4-(3-hydroxy-1-octyl)-Δ2-imidazoline, 1-methyl-2-(1-thia-4-carboxybutyl)-4-(3-hydroxy-1-octyl)-Δ2-imidazoline, 1-methyl-2-(1-thia-6-carboxyl-hexyl)-4-(3-hydroxy-1-octyl)-Δ2-imidazoline, 1-methyl-2-(1-thia-4-methoxycarbonyl-butyl)-4-(3-hydroxy-1-octyl)-Δ2-imidazoline, 1-methyl-2-(1-thia-5-methoxycarbonyl-pentyl)-4-(3-hydroxy-1-octyl)-Δ2-imidazoline, 1-methyl-2-(1-thia-4-methoxycarbonyl-butyl)-4-(3-hydroxy-5-(2-furyl)-1-pentyl)-Δ2-imidazoline, 1-methyl-2-(1-thia-4-methoxycarbonyl-butyl)-4-(3-hydroxy-4,4-dimethyl-4-cyclohexyloxy-1-butyl)-Δ2-imidazoline, 1-methyl-2-(1-thia-4-methoxycarbonyl-butyl)-4-(3-hydroxy-3-phenyl-1-propyl)-Δ2-imidazoline, 1-methyl-2-(1-thia-4-ethoxycarbonylbutyl)-4-(3-hydroxy-4-(3-trifluoromethyl-phenyloxy)-1-butyl)-Δ2-imidazoline, 1-methyl-2-(1-thia-4-cyclohexyloxycarbonyl-butyl)-4-(3-hydroxy-1-octyl)-Δ2-imidazoline, 1-methyl-2-(1-thia-7-methoxycarbonyl-heptyl)-4-(3-hydroxy-1-octyl)-Δ2-imidazoline, 1-methyl-2-(1-thia-4-ethoxycarbonyl-butyl)-4-(3-hydroxy-1-nonyl)-Δ2-imidazoline and 1-methyl-2-(1-thia-4-methoxycarbonylbutyl)-4-(3-hydroxy-1-decyl)-Δ2-imidazoline.

The compounds of the formula I are distinguished by an inhibiting action on platelet aggregation, relaxation of the vascular wall and hypotensive properties. They can therefore be used as medicaments. The compounds of the formula I are used as antihypertensive agents in a daily dose range of 0.01 mg/kg–0.5 mg/kg, preferably 0.05 mg/kg–0.1 mg/kg, on intravenous administration, or in a daily dose range of 0.05 mg/kg–2 mg/kg, preferably 0.1–1 mg/kg, on oral administration. The same daily doses as those stated above, and in some cases also lower dosages, are suitable for relaxation of the vascular wall, especially of the coronary arteries, and for inhibition of platelet aggregation.

The compounds can also be used in mammals, including humans and certain useful animals, for examples dogs and pigs, for reducing and controlling excessive secretion of gastric juice, the formation of gastrointestinal ulcers thereby being reduced or avoided and it being possible to accelerate the healing of such already existing ulcers. For this purpose, the compounds are injected or infused intravenously, subcutaneously or intramuscularly, in addition to oral use. The dosage plan for the prostacyclin in this treatment depends on various factors, including the nature, age, weight, sex and medical condition of the patient, and the dosage plan of the antiphlogistic synthetase inhibitor in respect of the action on the stomach/intestine. Thus, for example, not every patient requiring an antiphlogistic substance feels the same unpleasant gastrointestinal effects. Rather, these differ in type and degree. The physician or veterinary surgeon can thus establish, within his range of experience, whether the administration of the antiphlogistic substance produces undesirable gastrointestinal effects in the person or animal and can prescribe the effective amount of the prostaglandin with which these effects can be largely eliminated. Some representatives of this substance are suitable for the treatment of asthma. For example, they can be used as bronchodilators or as inhibitors of medicators, such as, for example, SRS-A and histamine, which are released from cells activated by an antigen/antibody complex. The compounds thus combat spasms and facilitate respiration in disease conditions such as bronchitis, pneumonia and emphysema. For these purposes, the compounds are administered in various dosage forms, for example orally in the form of tablets, capsules or liquids, rectally in the form of suppositories or parenterally, subcutaneously or intramuscularly, intravenous administration being preferred in emergency situations.

The compounds, of the formula I, according to the invention can be used as the free acids or in the form of their physiologically acceptable inorganic or organic salts or as esters. Acids and salts or esters can be used in the form of their aqueous solutions or suspensions or as solutions or suspensions in pharmacologically acceptable organic solvents, such as monohydric or polyhydric alcohols, such as, for example, ethanol, ethylene glycol or glycerol, in triacetin, in alcohol/acetaldehyde diacetal mixtures, oils, such as, for example, sunflower oil or codliver oil, ethers, such as, for example, diethylene glycol dimethyl ether or polyethers, such as, for example, polyethylene glycol, or in the presence of other pharmacologically acceptable polymeric carriers, such as, for example, polyvinylpyrrolidone.

The usual galenical infusion or injection solutions and tablets and formulations which can be used locally, such as creams, emulsions, suppositories or aerosols, are possible formulations.

The compounds of the formulae III–XII are novel useful intermediates for the preparation of compounds of the formula I.

EXAMPLE 1

1-Methyl-2-oxo-3-benzyloxycarbonyl-4-hydroxymethylimidazolidine III 16 g of 1-methyl-2-oxo-3-benzyloxy-carbonyl-4-carbomethoxy-imidazolidine (prepared as described by S. Saijo et al. in Chem. Pharm. Bull. 28, 1,459 (1980)) are dissolved in 550 ml of absolute methanol and the solution is cooled to 0° C., with stirring. 11 g of $NaBH_4$ in 110 ml of water at 0° C. are added in portions. When the addition has ended, the mixture is stirred at 0° C. for about 10 hours. Thin layer chromatography in $CH_2Cl_2$/MeOH 10:1. When the reaction has ended, the mixture is acidified to pH 3 with 2N HCl and concentrated in vacuo. The residue is taken up in $CH_2Cl_2$ and a little $H_2O$ is added. The phases are separated and the $H_2O$ phase is eluted 3 more times with $CH_2Cl_2$. The combined $CH_2Cl_2$ phases are dried with $MgSO_4$, filtered and concentrated in vacuo. Chromatography on silica gel with $CH_2Cl_2$:MeOH 20:1 as the eluting agent.

Yield: 12.3 g of n.H.V., melting point: 117° C., light crystals, (80% of theory) $C_{13}H_{16}O_4N_2$.

NMR: ($CDCl_3$) δ ppm 270 MHz: 2.85 (s, 3H) N—$CH_3$, 3.25–3.55(m, 2H)$CH_2OH$; 3.65–3.85 (m,2H)N—$CH_2$; 4.2–4.3(m,1H) N—CH<; 5.25(s,2H)$CH_2C_6H_5$ and 7.3–7.5(m,5H)$C_6H_5$.

Rf value: Methylene chloride/methanol 10:1=0.45.

EXAMPLE 2

1-Methyl-2-oxo-3-benzyloxycarbonyl-5-formyl-imidazolidine IV 0.7 ml (9.6 mmol) of absolute dimethylsulfoxide in 10 ml of absolute $CH_2Cl_2$ is cooled to −60° C. with the exclusion of moisture. 0.4 ml (4.4 mmol) of oxalyl chloride is added at this temperature and the mixture is stirred for about 10 minutes. 1.05 g (4 mmol) of 1-methyl-2-oxo-3-benzyloxycarbonyl-4-hydroxymethyl-imidazolidine (Example 1), dissolved in 10 ml of absolute $CH_2Cl_2$, are then added dropwise. Stirring is continued at −60° C. for 20 minutes. 2.7 ml of triethylamine are then added and the mixture is stirred for 30 minutes. It is then brought to pH at −10° to −20° C. with ethanolic HCl. Thin layer chromatography with $CH_2Cl_2$/MeOH 10:1. The reaction mixture is evaporated on a rotary evaporator. The crystalline residue is chromatographed on silica gel. Eluting agent: $CH_2Cl_2$/MeOH 10:1.

Yield: 950 mg, light oil, (90% of theory) $C_{13}H_{14}O_4N_2$, molecular weight 262.

NMR: ($CDCl_3$) δ ppm 60 MHz: (2.8 (s, 3H) N—$CH_3$; 3.2–3.9 (m, 3H) N—$CH_2$, OH; 4.1–4.9 (m, 1H)=CH—OH; 5.2 (s, 2H ($C_6H_5CH_2O$; 7.3 (s, 5H) $C_6H_5$; the aldehyde proton of the non-enolic aldehyde appears as a doublet at 9.6 ppm.

Rf value: Methylene chloride/methanol 10:1=0.65.

EXAMPLE 3a

1-Methyl-2-oxo-3-benzyloxymethyl-4-(3-oxo-octenyl)-imidazolidine VI 6.72 g of 1,8-diazabicyclo-(5,4,0)-undec-7-ene(DBU) are introduced into 40 ml of dimethoxyethane (DME). 9.8 g of 2-oxoheptyl-phosphonic acid dimethyl ester, dissolved in 100 ml of absolute DME, are added dropwise at room temperature. The mixture is stirred at room temperature for 30 minutes. 10.5 g of 1-methyl-2-oxo-3-benzyloxycarbonyl-4-formyl-imidazolidine (Example 2), dissolved in 100 ml of absolute DME, are then added dropwise. When the addition has ended, the mixture is stirred at room temperature for about 45 minutes. The mixture is then carefully brought to pH 7 with 2N HCl, while cooling with ice. The reaction mixture is concentrated, the residue taken up in ethyl acetate and the mixture is washed with NaCl solution. The ethyl acetate phase is dried and concentrated in vacuo. Crude yield: 15 g.

Column chromatography on $SiO_2$ with ethyl acetate as the eluting agent:

Yield: 7.5 g of light oil (53% of theory) $C_{20}H_{26}N_2O_4$, molecular weight=358.

NMR: ($CDCl_3$) δ ppm 60 MHz: 0.8–0.95 (t, 3H) $CH_3$; 1.1–1.7 (m, 6H) $CH_2$; 2.2–2.6 (m, 2H) $CH_2CO$; 2.85 (s, 3H) N—$CH_3$; 3.0–3.9 (m, 2H) N—$CH_2$; 4.5–5.0 (m, 1H) N—CH; 5.2 (s, 2H) $C_6H_5CH_2O$; 6.0–6.9 (ABX spectrum, 2H) CH=CH and 7.3 (s, 5H) $C_6H_5$.

Rf value: Ethyl acetate: 0.44 (can be stained with iodine).

EXAMPLES 3b–3i

The compounds 3b–3i can be prepared analogously to Example 3a from the corresponding phosphonates of the general formula V and 1-methyl-2-oxo-3-benzoyloxycarbonyl-5-formyl-imidazolidine IV (n=1).

| Example No. | Rf values Ethyl acetate | R² = | Yield % |
|---|---|---|---|
| (b) | 0.5 |  | 58 |
| (c) | 0.58 | 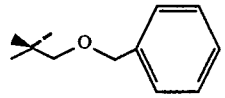 | 73 |
| (d) | 0.6 | 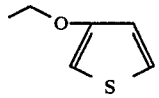 | 55 |
| (e) | 0.48 | 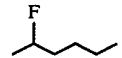 | 52 |
| (f) | 0.45 | 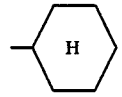 | 70 |
| (g) | 0.65 | 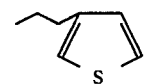 | 65 |
| (h) | 0.6 | 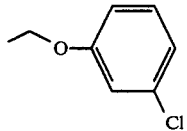 | 55 |
| (i) | 0.48 | 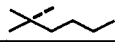 | 38 |

EXAMPLE 4

1-Methyl-2-oxo-3-benzoyloxymethyl-4-(3-hydroxy-octenyl)-imidazolidine VII 8.5 g of 1-methyl-2-oxo-3-benzoyloxymethyl-4-(3-oxo-octenyl)-imidazoline (Example 3) are dissolved in 250 ml of methanol and 140 ml of water. 3.8 g of sodium borohydride, dissolved in 100 ml of ice-water, are added at 0°, with stirring. The reaction has ended after 2–3 hours. The reaction mixture is acidified to pH 4 with 2N hydrochloric acid and then concentrated in vacuo. The residue is taken up in ethyl acetate, the mixture is washed with sodium chloride solution and the aqueous phase is extracted 3 times with ethyl acetate. The combined organic extracts are dried with MgSO₄, filtered and concentrated.

Yield: 8.0 g, light oil (96% of theory) $C_{20}H_{28}N_2O_4$, molecular weight=360.

NMR: (CDCl₃) δ ppm 60 MHz: 0.8–0.96 (t, 3H) CH₃; 1.0–1.8 (m, 8H) CH₂; 2.85 (s, 3H) N—CH₃; 3.0–3.7 (m, 2H); 3.9–4.2 (m, 1H) CH OH; 4.2–4.8 (m, 1H) N—CH; 5.2 (s, 2H) C₆H₅CH₂O; 5.55–5.7 (m, 2H) CH=CH; 7.25 (s, 5H) C₆H₅.

Rf value: Ethyl acetate: 3'β-epimer: 0.40, 3'α-epimer: 0.33.

Thin layer silica gel plates from Merck: development with iodine.

EXAMPLE 5

1-Methyl-2-oxo-4-(3-hydroxy-octenyl)-imidazolidine VIII 110 ml of 2N NaOH are added to 8 g of 1-methyl-2-oxo-3-benzoyloxycarbonyl-4-(3-hydroxy-octenyl)-imidazolidine (Example 4) in 250 ml of methanol at room temperature, with stirring, and stirring is continued for 4 hours. The reaction mixture is concentrated in vacuo and the residue is extracted several times with methylene chloride. The methylene chloride phase is washed with sodium chloride solution, dried with MgSO₄, filtered and concentrated in vacuo to give 8.3 of an oil. Column chromatography with silica gel 60 (Merck AG) 0.063–0.2 mm, eluting agent: ethyl acetate.

Yield: 4.9 g of light oil (97% of theory) $C_{12}H_{22}O_2N_2$, molecular weight=226.

NMR: (CDCl₃) δ ppm 60 MHz: 0.8–1.0 (t, 3H) CH₃; 1.0–1.7 (m, 8H) CH₂; 2.8 (s, 3H) N—CH₃; NHCO; 5.55–5.7 (m, 2H) CH=CH.

Rf value: Ethyl acetate: 3'β-epimer: 0.15, 3'α-epimer: 0.08.

EXAMPLE 6

1-Methyl-2-oxo-4-(3-acetoxy-octenyl)-imidazolidine X 5 g of 1-methyl-2-oxo-4-(3-hydroxy-octenyl)-imidazolidine (Example 5) are dissolved in 60 ml of pyridine, and a total of 10 ml of acetic anhydride are added in portions at room temperature in the course of 8 hours, with stirring and exclusion of moisture. The reaction mixture is poured onto ice-water and covered with a layer of ethyl acetate. The mixture is acidified to pH 3 with 2N HCl, with stirring. The organic phase is separated off and the aqueous phase is extracted several times with ethyl acetate. The combined organic extracts are dried with MgSO₄ and filtered and the solvent is removed in vacuo.

Yield: 5.3 g of light oil (89% of theory) $C_{14}H_{24}N_2O_3$, molecular weight=268.

NMR: (CDCl₃) δ ppm 270 MHz: 0.85 (t, 3H) CH₃, 1.2–1.4 (m, 8H) CH₂; 1.5–1.7 (m, 2H) CH₂; 2.05 (d, J=4 Hz, 3H) OAc; 2.75 (s, 3H) N—CH₃; 3.0 3.1/3.5–3.6 (m, 2H) N—CH₂; 4.1–4.25 (m, 1H) N—CH—C≡; 5.15–5.25 (m, 1H) CH≈OAc; 5.25–5.4 (broad s, 1H) NHCO; 5.6–5.7 (m, 2H) CH=CH.

Rf value: Ethyl acetate: 0.24.

EXAMPLE 7

1-Methyl-2-thioxo-4-(3-acetoxy-octenyl)-imidazolidine XI 500 mg of 1-methyl-2-oxo-4-(3-acetoxy-octenyl)-imidazolidine (Example 6) are dissolved in 15 ml of absolute toluene. After addition of 3 g of beach sand, the mixture is warmed to 90° C. in a stream of nitrogen. At this temperature, 3 times 250 mg of P₄S₁₀.anisole are added in portions and the mixture is stirred for 2–3 hours. The reaction mixture is filtered, the residue on the filter is washed with toluene and the toluene phase is concentrated in vacuo. The residue is chromatographed on a Merck prepacked column with silica gel 0.063–0.2 mm and cyclohexane/ethyl acetate=1:1 as the eluting agent.

Yield: 400 mg, melting point: 45° C., colorless crystals, (76% of theory) $C_{14}H_{24}SN_2O_2$, molecular weight 284.

NMR: (CDCl₃) δ ppm 60 MHz: 0.8–1.0 (t, 3H) CH₃; 1.0–1.8 (m, 8H) CH₂; (s, 3H) OAc; 3.1 (s, 3H) N—CH₃; 3.15–4.0 (m, 2H) N—CH₂; 4.0–4.5 (m, 1H) N—CH—C=; 5.0–5.4 (m, 1H) CH OAc; 5.6–5.7 (m, 2H) CH=CH; 5.7–6.0 (broad s, 1H) NHCS.

Rf value: Ethyl acetate: 0.88.

EXAMPLE 8

1-Methyl-2-thioxo-4-(3-hydroxy-octenyl)-imidazolidine XII 290 mg of 1-methyl-2-thioxo-4-(3-acetoxy-octenyl)-imidazolidine (Example 7) are dissolved in 20 ml of absolute methanol. 400 g of finely powdered anhydrous $K_2CO_3$ are added, with stirring. The mixture is stirred for several hours with exclusion of moisture. The reaction mixture is then brought to pH 6 with 2N acetic acid and concentrated in vacuo. The residue is taken up in ethyl acetate and the ethyl acetate phase is extracted with water, dried with $MgSO_4$, filtered and concentrated in vacuo.

Yield: 230 mg of light oil, (93% of theory) $C_{12}H_{22}SN_2O$, molecular weight=242.

NMR: (CDCl₃) δ ppm 60 MHz: 0.8–1.0 (m, 3H) CH₃; 1.0–1.8 (m, 8H) CH₂; s, 3H) N—CH₃; 3.1–4.0 (m, 3H) CH₂—N; 4.0–4.4 (m, 1H) CH OH; 5.6–5.7 (m, 2H) CH=CH; 5.6–6.1 (broad s, 1H) NHCS.

Rf value: Ethyl acetate: 3'β-epimer: 0.69, 3'α-epimer: 0.64.

EXAMPLE 9a

1-Methyl-2-(1-thia-4-ethoxycarbonyl-butyl)-4-(3-hydroxyoctenyl)-Δ2-imidazoline I (A=CH=CH, $R^1$=$C_2H_5$, $R^2$=$C_5H_{11}$, n=1)

180 mg of 1-methyl-2-thioxo-4-(3-acetoxy-octenyl)-imidazoline (Example 8) are dissolved in 5 ml of absolute diglyme and the solution is warmed to 90° C., with stirring and exclusion of moisture. After addition of 0.2 ml of ethyl 4-bromobutyrate, the mixture is stirred at 90° C. for 2 hours and a further 0.2 ml of ethyl 4-bromobutyrate is then added. After 4–5 hours at 90° C., the reaction has ended. Ethyl acetate is added to the reaction mixture and the mixture is washed with half-saturated $NaHCO_3$ solution. The organic phase is separated off, dried with $MgSO_4$, filtered and concentrated. It is chromatographed on silica gel with $CH_2Cl_2$:MeOH 20:1.

Yield: 161 mg (61% of theory). Fractions 95–175=86 mg (3'β-epimer), Rf value=0.18 ($CH_2Cl_2$:MeOH=10:1) light oil. Fractions 185–235=75 mg (3'α-epimer), Rf value=0.12 ($CH_2Cl_2$:MeOH=10:1) light oil. $C_{18}H_{32}N_2SO_3$, molecular weight 356.

NMR: (CDCl₃) 270 MHz δ values in ppm, spectra for the α- and β-epimers are identical in the context of the usual resolution: 0.85 (t, 3H) —CH₃; 1.25 (t, 3H) —OCH₂CH₃; 1.2–1.3 (m, 6H) CH₂; 1.4–1.6 (m, 2H) CH₂; 2.05 (p, 2H) S—CH₂—CH₂—CH₂—CO₂Et; 2.45 (t, 2H) CH₂CO₂Et; 2.85 (s, 3H) N—CH₃; 3.2 (t, 2H) S—CH₂; 3.3 (dd, 1H) 3.65 (d, 1H) N—CH₂; 4.1 (q, 2H) OCH₂CH₃; 4.1–4.2 (m, 1H) CH≈OH; 4.5–4.6 (m, 1H) N—CH—C=; 5.65–5.85 (m, 2H) CH=CH.

| Example No. 9 | NMR-data (ppm), characteristic signals | $R^2$ = | MS (molar mass) | $R_f$ values $CH_2Cl_2$/MeOH 10:1 α/β-Epimer | Yield % |
|---|---|---|---|---|---|
| b | δ = 0.9 (s, 6H) —C(CH₃)₂; 1.15 (t, 3H) —OCH₂CH₃; 3.3 (s, 2H) —OCH₂; 3.5 (q, 2H) OCH₂CH₃ | | $C_{19}H_{34}N_2SO_4$ 386.56 | 0.2/0.14 | 71 |
| c | δ = 0.9 (d, 6H) C(CH₃)₂; 7.2 (s, 5H) aromatic proton | | $C_{24}H_{36}N_2SO_4$ 448.63 | 0.25/0.18 | 65 |
| d | δ = 3.9 (d, 2H) CH₂O 6.1–7.3 (triple m, 3H) thiophene | | $C_{18}H_{26}N_2S_2O_4$ 398.55 | 0.4/0.33 | 53 |
| e | δ = 4.95 (m, 1H) >CH—F | | $C_{18}H_{31}N_2SO_3F$ 374.52 | 0.23/0.1 | 40 |
| f | δ = 1.1–2.0 (m, 11H) CH, CH₂; | | $C_{18}H_{32}N_2SO_3$ 356.53 | 0.17/0.13 | 81 |

-continued

| Example No. 9 | NMR-data (ppm), characteristic signals | R² = | MS (molar mass) | Rƒ-values CH₂Cl₂/MeOH 10:1 α/β-Epimer | Yield % |
| --- | --- | --- | --- | --- | --- |
| g | δ = 6.8–7.3 (m, 3H) thiophene | (CH₂CH₂-thiophene) | C₁₉H₂₈N₂S₂O₃ 396.58 | 0.42/0.35 | 62 |
| h | δ = 3.85 (d, 2H) —CH₂—O— 6.0–7.3 (m, 4H) aromatic protons | (CH₂CH₂-O-C₆H₄Cl) | C₂₀H₂₇N₂SO₄Cl 426.96 | 0.40/0.32 | 49 |
| i | δ = 0.85 (s, 6H) —C(CH₃)₂ | (neopentyl-type chain) | C₂₀H₃₆N₂SO₃ 384.59 | 0.2/0.12 | 53 |

EXAMPLE 10

1-Methyl-2-oxo-4-(3-hydroxy-octyl)-imidazolidine IX- 3.1 g of Pd/C (10% strength) are added to 5.4 g (15 mmol) of 1-methyl-2-oxo-3-benzoyloxymethyl-4-(3-hydroxyoctenyl)-imidazolidine (Example 4) in 0.20 liters of methanol and the mixture is hydrogenated with hydrogen in a shaken flask under normal pressure. After the calculated amount of hydrogen has been absorbed, the catalyst is filtered off and the filtrate is concentrated.

Yield: 3.1 g of a light oil, (93% of theory) $C_{12}H_{24}N_2O_2$, molecular weight=226.

NMR: (CDCl₃) δ ppm 60 MHz 0.8–1.0 (t, 3H) CH₃; 1.0–1.8 (m, 12H) CH₂; 2.7 (s, 3H, N—CH₃; 3.0–3.7 (m, 3H) N—CH₂ N—CH; 3.9–4.1 (m, 1H) CH∼OH; 5.7–5.9 (broad s, 1H) NHCO.

Rf value: CH₂Cl₂/CH₃OH 20:1=0.36.

EXAMPLE 11

1-Methyl-2-oxo-4-(3-acetoxy-octyl)-imidazolidine X 12,8 g (75 mmol) of 1-methyl-2-oxo-4-(3-hydroxyoctyl)-imidazoline (Example 10) are dissolved in 100 ml of absolute pyridine. 6 ml (62 mmol) of acetic anhydride (freshly distilled) are then added in portions at room temperature and the mixture is stirred at room temperature for 2 days. The pyridine is removed in vacuo and the residue is dissolved in ethyl acetate and extracted 3 times with sodium chloride solution. The organic phase is dried with MgSO₄ and concentrated in vacuo. The residue is chromatographed by column chromatography on silica gel with CH₂Cl₂/MeOH=20:1 as the eluting agent.

Yield: 12.3 g of a light yellow oil, (80% of theory) $C_{14}H_{26}N_2O_3$, molecular weight=270.

NMR: (CDCl₃) δ ppm 60 MHz 0.8–1.0 (t, 3H) CH₃; 1.0–1.8 (m, 12H) CH₂; 2.0 (s, 3H) COCH₃; 2.7 (s, 3H) N—CH₃; 3.0–3.7 (m, 3H) N—CH₂; N-CH; 4.6–5.0 (m, 1H) CH∼OAc; 5.7–5.9 (broad s, 1H) NHCO.

Rf value: Methylene chloride/methanol 20:1=0.54.

EXAMPLE 12

1-Methyl-2-thioxo-4-(3-acetoxy-octyl)-imidazolidine XI 2.5 g (9.2 mmol) of 1-methyl-2-oxo-4-(3-acetoxyoctyl)-imidazolidine (Example 11) are dissolved in 80 ml of absolute toluene, 10 g of beach sand are added and the mixture is warmed to 90° C., with stirring. 2.50 g of P₄S₁₀.anisole are then added and stirring is continued at 90° C. for 2 hours. The reaction mixture is filtered, the residue on the filter is washed with toluene and the toluene phase is concentrated. The residue is chromatographed on silica gel in cyclohexane/ethyl acetate 1:1.

Yield: 2.5 g of a light oil; (95% of theory) $C_{14}H_{26}N_2SO_2$, molecular weight=286.

NMR: (CDCl₃) δ ppm 60 MHz 0.8–1.0 (t, 3H) CH₃; 1.0–1.8 (m, 12H) CH₂; 2.0 (s, 3H) COCH₃; 3.1 (s, 3H) N—CH₃; 3.1–3.9 (m, 3H) CH₂N, >CH—N; 4.6–5.1 CH∼OAc; 5.9–6.2 (broad s, 1H) CSNH.

Rf value: Ethyl acetate: 0.84.

EXAMPLE 13

1-Methyl-2-thioxo-4-(3-hydroxy-octyl)-imidazolidine XII 280 mg of 1-methyl-2-thioxo-4-(3-ace-toxy-octyl)-imidazolidine (Example 12) is dissolved in 20 ml of absolute MeOH, and 300 mg of powdered K₂CO₃ are added. The mixture is stirred at room temperature for 3 hours. When the reaction has ended, the reaction mixture is brought to pH 6 with 2N acetic acid and concentrated. The residue is taken up in ethyl acetate and extracted with H₂O. The dried (MgSO₄) ethyl acetate phase is concentrated.

(Yield: 220 mg of a light oil, (92% of theory) $C_{12}H_{24}N_2SO$, molecular weight=224.

NMR: (CDCl₃) δ ppm MHz 0.8–1.0 (t, 3H) CH₃; 1.0–1.8 (m, 12H) CH₂; 3.1 (s, 3H) N—CH₃; 3.1–3.9 (m, 3H) N—CH₂, N—CH; 6.1–6.5 (broad double band, 1H) NHCS.

Rf value: Ethyl acetate 0.59.

EXAMPLE 14a

1-Methyl-2-(1-thia-4-ethoxycarbonyl-butyl)-4-(3-hydroxyoctyl)-Δ2-imidazoline I (A=CH₂CH₂, R¹=C₂H₅, R²=C₅H₁₁, n=1)

180 mg (73.8 mmol) of 1-methyl-2-thioxo-4-(3-hydroxy-octyl)-imidazolidine (Example 13) are warmed to 90° C. in 5 ml of absolute diglyme, with stirring and exclusion of moisture, and 0.2 ml of ethyl 4-bromobutyrate is added. The mixture is then stirred for 4 hours, a further 0.2 ml of ethyl 4-bromobutyrate is again added at 90° C. and stirring is continued at 90° C. for 3 hours. The reaction solution is dissolved in 20 ml of ethyl acetate and the solution is washed with NaHCO₃ solution. The ethyl acetate phase is dried with MgSO₄, filtered and concentrated in vacuo.

Crude yield: 0.2 g of a light oil. Chromatographed over a Merck prepacked column, size β/silica gel (particle size 0.063–0.2 mm) with methylene chloride/CH$_3$OH 10:1 as the eluting agent: Fractions 145–250=125 mg (3'β-epimer), Rf value=0.15 (CH$_2$Cl$_2$/CH$_3$OH 10:1). Fractions 255–360=95 mg (3'α-epimer), Rf value=0.12 (CH$_2$Cl$_2$/CH$_3$OH 10:1).

Yield: C$_{13}$H$_{34}$N$_2$SO$_3$, molecular weight=358, 220 mg (83% of theory) of a light oil.

NMR (CDCl$_3$): 270 MHz

δ ppm spectra for the α- and β-epimers are identical in the context of the usual resolution: 0.9 (t,3H) CH$_3$; 1.26 (t,3H) COOCH$_2$—CH$_3$; 1.2–1.85 (m,12H) —CH$_2$—; 2.03 (p,2H)—s—$\overline{CH_2}$—CH$_2$—CH$_2$—CO$_2$Et; 2.45 (t,2h) CH$_2$—CO$_2$Et; 2.75 ($\overline{d,3H}$) N—CH$_3$; 3.1 (t,3H)—s—CH$_2$—$\underline{CH_2}$; 3.9 (q, 1H) N—CH$_2$; 3.45–3.6 (m, 1H) N—CH$_2$; $\overline{3.6}$–3.7 (m, 1H) CH~OH; 3.8–4.0 (m, 1H)=N—CH; 4.1 (q, 2H) O$\underline{CH_2}$CH$_3$.

EXAMPLES 14b–14i

The compounds 14b–14i (formula I, n=1, for R$^2$ see Table) can be prepared analogously to Example 3a from the compounds of Examples 3b–3i applying the instructions given in Example 4 and in Examples 10–14a.

EXAMPLE 15a

The sodium salt of 1-methyl-2-(1-thia-4-carboxy-butyl)-4-(3-hydroxy-octyl)-Δ2-imidazoline I (A=CH$_2$CH$_2$, R$^1$=Na, R$^2$=C$_5$H$_{11}$, n=1)

58 mg (1 mmol) of 1-methyl-2-(1-thia-4-ethoxycarbonylbutyl)-4-(3-hydroxy-1-octyl)-Δ2-imidazolidine (Example 14a) are dissolved in 6 ml of 80% strength ethanol. A solution of 13 mg of sodium in 4 ml of ethanol/4 ml of H$_2$O is added to this solution, with stirring. The mixture is stirred at +10° C. under argon for 3 hours, the solution is filtered over active charcoal and the solvent is removed in vacuo at 10° C. (freeze-drying). The sodium salt I is obtained as a light powder.

IR band: KBr trituration: COO$^\ominus$ 1609 cm$^{-1}$.

| Example No. 14 | NMR-data (ppm), characteristic signals | R$^2$ = | MS (molar mass) | R$_f$-values CH$_2$Cl$_2$/MeOH 10:1 α/β-Epimer | Yield % |
|---|---|---|---|---|---|
| b | δ = 0.9 (s, 6H) —C(CH$_3$)$_2$; 1.15 (t, 3H) —OCH$_2$C$\underline{H}_3$; 3.3 (s, 2H) —OCH$_2$; 3.5 (q, 2H) OC$\underline{H}_2$CH$_3$ | | C$_{19}$H$_{36}$N$_2$SO$_4$ 388.58 | 0.17/0.15 | 79 |
| c | δ = 0.9 (d, 6H) C(CH$_3$)$_2$; 7.2 (s, 5H) aromatic proton | | C$_{24}$H$_{38}$N$_2$SO$_4$ 450.65 | 0.25/0.2 | 83 |
| d | δ = 3.9 (d, 2H) CH$_2$O 6.1–7.3 (triple m, 3H) thiophene | | C$_{18}$H$_{28}$H$_2$N$_2$S$_2$O$_4$ 400.57 | 0.5/0.42 | 60 |
| e | δ = 4.95 (m, 1H) CH—F | | C$_{18}$H$_{33}$N$_2$SO$_3$F 376.54 | 0.19/0.15 | 45 |
| f | δ = 1.1–2.0 (m, 11H) CH, CH$_2$ | | C$_{18}$H$_{34}$N$_2$SO$_3$ 358.55 | 0.16/0.14 | 80 |
| g | δ = 6.8–7.3 (m, 3H) thiophene | | C$_{19}$H$_{30}$N$_2$S$_2$O$_3$ 398.60 | 0.52/0.44 | 65 |
| h | δ = 3.85 (d, 2H) —CH$_2$—O— 6.0–7.3 (m, 4H) aromatic proton | | C$_{20}$H$_{29}$N$_2$SO$_4$Cl 428.98 | 0.48/0.4 | 72 |
| i | δ = 0.85 (s, 6H) —C(CH$_3$)$_2$— | | C$_{20}$H$_{38}$N$_2$SO$_3$ 386.61 | 017/0.14 | 53 |

EXAMPLE 15b

The potassium salt of 1-methyl-2-(1-thia-4-carboxy-butyl)-4-(3-hydroxy-1-octenyl)-Δ2-imidazoline I (A=CH=CH, $R^1$=K, $R^2$=$C_5H_{11}$, n=1)

35 mg of pure 1-methyl-2-(1-thia-4-ethoxycarbonyl-butyl)-4-(3-hydroxy-1-octenyl)-Δ2-imidazoline (Example 9a), 0.2 ml of 0.5M potassium hydroxide solution and 2 ml of methano are left to stand under an inert gas at room temperature for 24 hours. The methanol is stripped off in vacuo and the aqueous solution of the potassium salt is freeze-dried. The potassium salt I is obtained as a colorless powder.

IR band: KBr trituration: —COO$^\ominus$ 1605 cm$^{-1}$.

EXAMPLE 15c

The triethylammonium salt of 1-methyl-2-(1-thia-4-carboxybutyl)-4-(3-hydroxy-1-octenyl)-Δ2-imidazoline I (n=1, $R^1$=HN$^\oplus$($C_2H_5$)$_3$, $R^2$=$C_5H_{11}$, A=CH=CH)

An aqueous solution of 100 mg of the potassium salt of Example 15b is introduced onto a column with 15 g of ®Amberlite CG-50 (triethylammonium form). The column is eluted with a 3% strength aqueous solution of triethylammonium carbonate. By freeze-drying the eluate, the product is obtained as a crystalline powder.

IR band: KBr trituration: —COO$^\ominus$ 1600 cm$^{-1}$ (decomposition 80° C.).

Analogously to Examples 15a to 15c, the corresponding alkali metal or ammonium salts can be prepared from the compounds of Examples 9b to 9i or 14b–14i by alkaline ester hydrolysis and, if appropriate, chromatography on ion exchangers.

EXAMPLE 16

1-Methyl-2-(1-thia-4-isopropyloxycarbonyl-butyl)-4-(3-hydroxy-4,4-dimethyl-1-octenyl)-Δ1-pyrroline I (n=1, $R^1$=CH($CH_3$)$_2$, $R^2$=—C($CH_3$)—$C_4H_9$—n, A=CH=CH)

170 mg (1 mmol) of 1-methyl-2-(1-thia-4-ethoxycarbonyl-butyl)-4-(3-hydroxy-1-octenyl)-Δ2-imidazoline (Example 9a) are dissolved in 15 ml of absolute isopropanol, and 50 mg of powdered and thoroughly dried potassium carbonate are added. The mixture is stirred for 1 hour. The solvent is stripped off in vacuo, the residue is taken up in ethyl acetate, the ethyl acetate phase is washed with water and dried and the solvent is removed in vacuo.

Yield: 345 mg of a light oil. 3'β-epimer: Rf value in cyclohexane/ethyl acetate 1:1=0.75. 3'α-epimer: Rf value in cyclohexane/ethyl acetate 1:1=0.68.

NMR (CDCl$_3$): δ ppm: 4.95 (septett,1H) C$\underline{H}$(CH$_3$)$_2$ and 1.2 (d,6H) CH(C$\underline{H}_3$)$_2$.

We claim:

1. A compound of the formula I

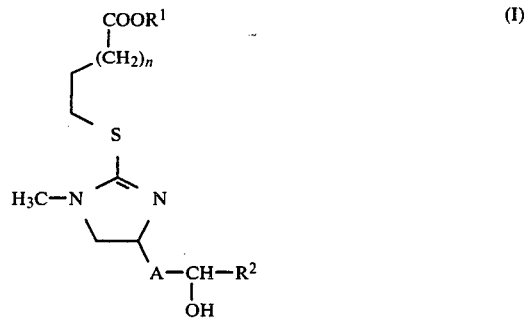

in which
R$^1$ denotes hydrogen, a straight-chain or branched alkyl radical with up to 8 carbon atoms, a straight-chain or branched unsaturated aliphatic hydrocarbon radical with 3–6 carbon atoms, a cycloaliphatic hydrocarbon radical with 3–7 carbon atoms, an araliphatic hydrocarbon radical with 7–9 carbon atoms or a physiologically acceptable metal ion, NH$_4$ ion or an ammonium ion which is derived from a primary, secondary or tertiary amine, or a tetraalkylammonium ion, R$^2$ denotes a phenyl radical, which can be mono-, di- or tri-substituted in the nucleus by halogen, trifluoromethyl, alkyl with 1–6 carbon atoms or alkoxy with 1–6 carbon atoms, or denotes a cycloaliphatic radical with 3–8 carbon atoms, a straight-chain or branched alkyl radical with up to 8 carbon atoms or a straight-chain or branched unsaturated aliphatic hydrocarbon radical with 3–8 carbon atoms, it being possible for the aliphatic radicals in turn to be substituted by (a) a straight-chain or branched alkoxy radical with up to 6 carbon atoms or a straight-chain or branched alkenyloxy or alkinyloxy radical with 3–6 carbon atoms, (b) halogen, cycloalkyl with 3–7 carbon atoms, an unsubstituted phenyl, α- or β-thienyl or α- or β-furyl radical or a phenyl, thienyl or furyl radical which is in turn mono-, di- or tri-substituted in the nucleus by halogen, trifluoromethyl, alkyl with 1–6 carbon atoms or alkoxy with 1–6 carbon atoms, (c) an unsubstituted phenoxy, α- or β-thienyloxy or cycloalkoxy radical with 3–7 carbon atoms, or a phenoxy, α- or β-thienyloxy or cycloalkoxy radical with 3–7 carbon atoms, which is in turn mono-, di- or tri-substituted in the ring by halogen, trifluoromethyl or alkoxy with 1–6 carbon atoms, A denotes a —CH=CH— or —CH$_2$—CH$_2$— group and n denotes the number 0, 1, 2, 3 or 4.

2. A compound of the formula I as claimed in claim 1, in which R$^1$ denotes hydrogen, C$_1$–C$_4$-alkyl, C$_2$–C$_4$-alkenyl, C$_5$–C$_7$-cycloalkyl, phenethyl, benzyl or an ammonium ion which is derived from a primary, secondary or tertiary amine, R$^2$ denotes unsubstituted phenyl or phenyl which is mono-substituted by halogen, trifluoromethyl, C$_1$–C$_4$-alkyl or C$_1$–C$_4$-alkoxy, or denotes unsubstituted C$_3$–C$_7$-alkyl or C$_3$–C$_7$-alkyl which is substituted by C$_5$–C$_7$-cycloalkyl, C$_1$–C$_3$-alkoxy, phenoxy, halogenophenoxy, thienyloxy, halogenothienyloxy, cyclohexyloxy, thienyl, halogenothienyl or furyl, A represents a —CH=CH— or —CH₂—CH₂— group and n represents the number 1 or 2.

3. A pharmaceutical composition comprising a therapeutically effective amount of a compound of the formula I as recited in claim 1 and a pharmaceutically acceptable excipient for use as a hypotensive, vascular wall relaxant, platelet-aggregating inhibiting, gastric juice inhibiting, or bronchodilating agent.

4. A pharmaceutical composition according to claim 3 which further comprises a stabilizer.

5. A method for treating hypertension which comprises administering a compound recited in claim 1 in a therapeutically effective amount to a patient suffering from hypertension.

6. A method for treating hypertension according to claim 5 which further comprises orally administering said compound in a daily dosage of 0.05 mg/kg to 2 mg/kg.

7. A method for treating hypertension according to claim 5 which further comprises intravenously administering said compound in a daily dosage of 0.01 mg/kg to 0.5 mg/kg.

8. A method for relaxation of the vascular walls which comprises administering a compound recited in claim 1 in a therapeutically effective amount to a patient.

9. A method for relaxing vascular walls according to claim 8 which further comprises orally administering said compound in a daily dosage of 0.05 mg/kg to 2 mg/kg.

10. A method for relaxing vascular walls according to claim 8 which further comprises intravenously administering said compound in a daily dosage of 0.01 mg/kg to 0.5 mg/kg.

11. A method for the inhibition of platelet aggregation which comprises administering a compound recited in claim 1 in a therapeutically effective amount to a patient.

12. A method for inhibiting platelet aggregation according to claim 11 which further comprises orally administering said compound in a daily dosage of 0.05 mg/kg to 2 mg/kg.

13. A method for inhibiting platelet aggregation according to claim 11 which further comprises intravenously administering said compound in a daily dosage of 0.01 mg/kg to 0.5 mg/kg.

* * * * *